United States Patent [19]

Freedman

[11] 3,972,887

[45] Aug. 3, 1976

[54] PROCESS FOR PREPARING PHOSPHOROTHIOATES AND PHENYLPHOSPONOTHIOATES

[75] Inventor: Harold H. Freedman, Newton Center, Mass.

[73] Assignee: The Dow Chemical Company, Midland, Mich.

[22] Filed: June 12, 1975

[21] Appl. No.: 586,441

Related U.S. Application Data

[63] Continuation of Ser. No. 397,513, Sept. 17, 1973, abandoned, which is a continuation-in-part of Ser. No. 207,535, Dec. 13, 1971, abandoned.

[30] Foreign Application Priority Data

Dec. 12, 1972 Italy ............................. 054615/72

[52] U.S. Cl. .................. 260/294.8 K; 260/250 B; 260/251 P; 260/297 P; 260/973
[51] Int. Cl.² ..................................... C07D 213/44
[58] Field of Search ............................ 260/294.8 K

[56] References Cited

FOREIGN PATENTS OR APPLICATIONS 1,227,144  4/1971  United Kingdom ............... 260/454

OTHER PUBLICATIONS

Chem. Abstracts, Seventh Collective Index, Subjects A–Amm, p. 1533S.
Starks, J.P.C.S., vol. 93 (1), pp. 195–199, (1971).
Starks et al., J.A.C.S., vol. 95 (11), pp. 3613–3617, (1973).
Hennis et al., I & E.C., Product Research & Development, vol. 6 (3), pp. 193–195, (1967).
Hennis et al., I & E.C., Product Research, vol. 7 (2), pp. 96–101, (1968).

*Primary Examiner*—Alan L. Rotman
*Attorney, Agent, or Firm*—L. Wayne White

[57] ABSTRACT

Quaternary ammonium salts are novel catalysts in the process of reacting an alkali metal phenate, pyridinate or pyrimidinate with an O,O-dialkyl phosphorochloridothioate or O-alkyl phenylphosphonochloridothioate to produce the corresponding phosphorothioates and phenylphosphonothioates. The process is conducted under alkaline conditions in a liquid reaction medium. As an example, O,O-diethyl O-(3,5,6-trichloro-2-pyridyl)-phosphorothioate is prepared in excellent yields and purity by reacting solid particulate sodium 3,5,6-trichloropyridinate with O,O-diethyl phosphorochloridothioate dissolved in a stirred methylene chloride reaction medium in the presence of a catalytic amount of benzyltriethylammonium chloride.

12 Claims, No Drawings

PROCESS FOR PREPARING PHOSPHOROTHIOATES AND PHENYLPHOSPONOTHIOATES

CROSS-REFERENCE TO RELATED APPLICATION

This is a continuation of application Ser. No. 397,513 filed Sept. 17, 1973, now abandoned, which-in-turn is a continuation-in-part of my U.S. patent application Ser. No. 207,535 filed Dec. 13, 1971, now abandoned.

BACKGROUND OF THE INVENTION

The O-pyridyl phosphates and phosphorothioates were described by Rigterink in U.S. Pat. No. 3,244,586. Such compounds are particularly useful as insecticides and biocides. They are represented by Formula (I)

$$R-O-\overset{Z}{\underset{R'}{P}}-R' \qquad (I)$$

wherein R represents halopyridyl, Z represents oxygen or sulfur and each R' independently represents lower alkyloxy, amino or lower alkylamino. Rigterink disclosed several methods for preparing the compounds but his preferred method comprised reacting a phosphorochloridate or phosphorochloridothioate of Formula (II)

$$Cl-\overset{Z}{\underset{R'}{P}}-R' \qquad (II)$$

with an alkali metal or tertiary amine salt of a halopyridinol having the formula R-O-alkali metal or R—OH tertiary amine. The disclosed methods were carried out in an inert organic liquid under anhydrous conditions. In each of the disclosed processes an alkali metal chloride or the tertiary amine hydrochloride salt is produced as a reaction byproduct which is removed by filtration. The disclosure of U.S. Pat. No. 3,244,586 is incorporated herein by reference.

Other phosphorothioates and phenylphosphonothioates have been similarly prepared and used. See, for example, the articles by O. Johnson in *Chemical Week*, pages 18–46 (26 July 1972) and by E. E. Kenaga and W. E. Allison in the *Bulletin of the Entomological Society of America*, Vol. 15, No. 2, pages 85-148 (June, 1969) which list many commercially available phosphorothioates and phenylphosphonothioates and which include U.S. patents pertaining to such compounds.

The phosphorothioates and phenylphosphonothioates referred to above and herein prepared correspond to the formula

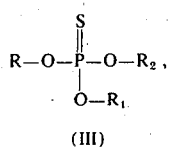 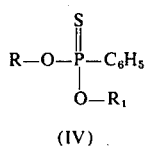

(III) (IV)

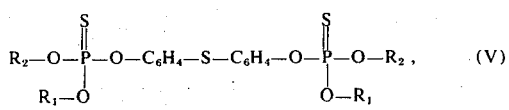

(V)

wherein:
$R_1$ and $R_2$ are each independently lower alkyl; and

R is 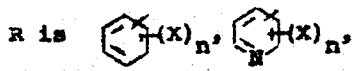

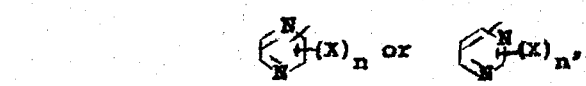

wherein:
n is 0, 1, 2 or 3; and
X is nitro, cyano, halo, (fluoro, chloro, bromo and iodo, inclusive), lower alkyl, lower alkoxy, lower alkylthio or lower alkylsulfinyl, with the proviso that R does not bear more than one nitro group, lower alkylthio group or lower alkylsulfinyl group.

By "lower alkyl" is meant in all instances alkyl of 1 to 4 carbon atoms (i.e. methyl, ethyl, propyl and butyl).

SUMMARY OF THE INVENTION

I have discovered that quaternary ammonium salts are novel catalysts in the process of making phosphorothioates and phenylphosphonothioates by reacting (a) an alkali metal phenate, pyridinate or pyrimidinate in solid particulate form with (b) an O,O-dialkyl phosphorochloridothioate or an O-alkyl phenylphosphonochloridothioate dissolved in an inert organic liquid reaction medium. The desired products are obtained in high yields and purity. The products are easily recovered from the reaction mixture with no contaminated waste streams to contend with.

Essentially any compound from the known class of quaternary ammonium compounds can be used in the instant invention. Suitable quaternary ammonium salts have a minimum solubility of at least about 1 weight percent in the liquid reaction medium at 25°C. and normally have a total aggregate carbon content of at least about 10 carbon atoms and preferably have from about 12 to about 31 carbon atoms. The ammonium salts can be represented by the formula $R_1'R_2'R_3'R_4'N^+A^-$ (VI), wherein $R_1'-R_4'$ are hydrocarbyl groups (e.g., alkyl, aryl, alkaryl, aralkyl, cycloalkyl, etc.) and $R_1'$ can join with $R_2'$ to form a 5- or 6-membered heterocyclic compound having at least one quaternized nitrogen atom in the ring and may also contain one atom of nitrogen, oxygen or sulfur within the ring. Typically, $R_1'-R_4'$ are hydrocarbyl groups of from 1 to about 12 carbon atoms. $A^-$ is a neutralizing anion and may be varied to convenience. Chloride and bromide are the preferred anions, but other illustrated anions include fluoride, iodide, tosylate, acetate, bisulfate, etc. The following compounds are illustrative: tetra-alkyl ammonium salts, such as tetramethyl-, tetraethyl-, tetra-n-butyl-, tetrahexyl-, methyltriethyl-, and trioctylmethyl- and tridecylmethyl-ammonium chlorides, bromides, iodides, bisulfates, tosylates, etc.; aralkylammonium salts, such as tetrabenzylammonium chloride, benzyltrimethyl-, benzyl-triethyl-, benzyltributyl-, and phenethyltrimethyl-ammonium chlorides, bromides, iodides, etc.; arylammonium salts, such as triphenylmethylammonium fluoride, chloride or bromide, N,N,N-trimethylanilinium chloride, N,N,N-triethylanilinium bromide, N,N-diethyl-N-ethylanilinium bisulfate, trimethylnaphthylammonium chloride, p-methylphenyltrimethylammonium chloride or tosylate, etc.; 5- and 6-membered heterocyclic compounds containing at least one quaternized nitrogen atom in the ring, such as N,N,N',N'-tetramethylpiperazinium dichloride, N-methylpyridinium chloride, N-hexylpyridinium iodide, 4-pyridyltrimethylammonium iodide, 1-methyl-1-azoniabicyclo-[2.2.1]heptane bromide, N,N-dibutylmorpholinium chloride, N-ethylthiazolium chloride, N-butylpyrrolium chloride, etc., and other like compounds.

The preferred catalysts are benzyltrimethyl-, benzyltriethyl- and tetra-n-butylammonium salts. The most preferred catalysts are triethylammonium chloride and tetra-n-butylammonium bisulfate.

The quaternary ammonium salts are used in the process in small but catalytic amounts. For example, amounts from about 0.25 to about 20 mole percent, based on the reactants, are suitable but amounts of from about 0.5 to about 10 mole percent are generally preferred.

The reaction proceeds at a satisfactory rate at temperatures of from about 0°C up to about 100°C with a preferred rate being obtained at temperatures of about 40°–60°C. The reaction pressure is not critical and generally atmospheric or superatmospheric pressures are used as a matter of convenience. Under the above conditions, reaction times of up to 8 hours are common although reaction times of from 0.25 to 5 hours are generally sufficient for the reaction to be substantially complete.

The process is typically conducted in a liquid reaction medium as a convenient means of controlling the reaction temperature. Suitable such inert organic liquids include chlorinated hydrocarbons, such as methylene chloride ($CH_2Cl_2$), chloroform, carbon tetrachloride and other like chlorinated hydrocarbons and hydrocarbons, such as benzene, toluene, cyclohexane, and the like. Methylene chloride is the preferred reaction medium diluent.

The process is conducted under alkaline conditions. Such conditions can be easily achieved by conventional methods, e.g., by conducting the process in the presence of caustic, or other base or by use of an appropriate buffer system.

Agitation (e.g., stirring, swirling, etc.) of the reaction mixture is advantageous, particularly when the process is conducted in the 2-phase liquid reaction medium.

The Reactants

The alkali metal phenates, pyridinates and pyrimidinates are known classes of compounds corresponding to the formulas $$R-O^-M^+ \quad \text{and} \quad M^+{}^-O-C_6H_4-S-C_6H_4-O^-M^+ ,$$

(VII)          (VIII)

wherein R has the above meaning and M is an alkali metal (Li, Na, K, etc.) but is preferably sodium or potassium and is most preferably sodium.

The O,O-dialkyl phosphorochloridothioates and O-alkyl phenylphosphonochloridothioates are likewise well known classes of compounds which correspond to the formulas

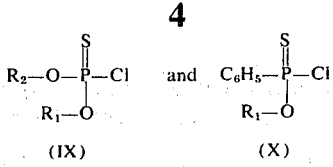

(IX)          (X)

wherein $R_1$ and $R_2$ are each independently lower alkyl but are preferably methyl or ethyl.

Various phosphorothioates and phenylphosphonothioates can obviously be prepared by using various combinations of the above reactants. Representative and illustrative lists of suitable reactants and combinations thereof are shown in Tables 1 and 2 below:

Table 1

$$R_2-O-\underset{R_1-O}{\overset{\overset{S}{\|}}{P}}-Cl + R-O^-M^+ \rightarrow R-O-\underset{O-R_1}{\overset{\overset{S}{\|}}{P}}-O-R_2$$

| No. | $R_1$ | $R_2$ | R | M |
|---|---|---|---|---|
| 1 | $CH_3$ | $CH_3$ | 3,5,6-trichloro-2-pyridyl | Na |
| 2 | $C_2H_5$ | $C_2H_5$ | 3,5,6-trichloro-2-pyridyl | Na |
| 3 | $C_2H_5$ | $C_2H_5$ | 3-fluoro-2-pyridyl | Na |
| 4 | $CH_3$ | $CH_3$ | 2,4,5-trichlorophenyl | Na |
| 5 | $C_2H_5$ | $C_2H_5$ | 2,4-dichlorophenyl | K |
| 6 | $CH_3$ | $CH_3$ | 2,5-dichloro-4-iodophenyl | Na |
| 7 | $CH_3$ | $CH_3$ | 2-chloro-4-nitrophenyl | Na |
| 8 | $C_2H_5$ | $C_2H_5$ | 4-nitrophenyl | Na |
| 9 | $CH_3$ | $CH_3$ | 4-nitrophenyl | K |
| 10 | $CH_3$ | $CH_3$ | 3-methyl-4-nitrophenyl | K |
| 11 | $CH_3$ | $CH_3$ | 3-methyl-4-(methylthio)phenyl | Na |
| 12 | $C_2H_5$ | $C_2H_5$ | 3-methyl-4-(methylsulfonyl)phenyl | Na |

Table 1-continued $$R_2-O-\overset{\overset{S}{\|}}{\underset{R_1-O}{P}}-Cl + R-O^-M^+ \rightarrow R-O-\overset{\overset{S}{\|}}{\underset{O-R_1}{P}}-O-R_2$$

| No. | R₁ | R₂ | R | M |
|---|---|---|---|---|
| 13 | C₂H₅ | C₂H₅ | -⟨C₆H₄⟩-S(O)-CH₃ | Na |
| 14 | C₂H₅ | C₂H₅ | -⟨pyrimidine⟩-CH(CH₃)₂ | K |
| 15 | C₂H₅ | C₂H₅ | -⟨pyrazine⟩ | Na |
| 16 | CH₃ | CH₃ | -⟨C₆H₄⟩-CN | K |

Table 2

$$C_6H_5-\overset{\overset{S}{\|}}{\underset{R_1-O}{P}}-Cl + R-O^-M^+ \rightarrow R-O-\overset{\overset{S}{\|}}{\underset{O-R_1}{P}}-C_6H_5$$

| No. | R₁ | R | M |
|---|---|---|---|
| 17 | CH₃ | -⟨C₆H₂⟩(Cl)(Br)(Cl) | Na |
| 18 | C₂H₅ | -⟨C₆H₄⟩-NO₂ | K |
| 19 | C₂H₅ | -⟨C₆H₄⟩-CN | Na |

The compounds of Formula (V) are prepared in like manner.

E.g. $2(CH_3O)_2\overset{\overset{S}{\|}}{P}-Cl + [Na^+{}^-O-C_6H_4]_2S \rightarrow$ $\rightarrow [(CH_3O)_2\overset{\overset{S}{\|}}{P}O-C_6H_4]_2S$ The following examples further illustrate the invention.

EXAMPLE 1

O,O-Diethyl phosphorochloridothioate (9.5 g., 0.05 mole) and benzyltriethylammonium chloride (2.0 g.) were added to sodium 3,5,6-trichloro-2-pyridinate (12.0 g., 0.05 mole) dispersed in 50 ml. of methylene chloride. The mixture was warmed at reflux temperature for 2 hours, cooled, and filtered to remove the solid by-product NaCl. The solvent was removed from the filtrate under reduced pressure and the oily residue washed three times with 25 ml. portions of cold water. The resulting white solid was dried and identified as O,O-diethyl O-3,5,6-trichloro-2-pyridyl phosphorothioate. The product (15.5 g.) melted at 35°-7°C.

EXAMPLES 2-4

Using substantially the same procedure of Example 1, a series of experiments were conducted using other quaternary ammonium catalysts. The product in each instance was of excellent purity. The results are summarized in Table I below.

Table 3

| Ex. | Catalyst (mole %) | Time (Hrs.) | Yield (%)* |
|---|---|---|---|
| 2 | C₆H₅CH₂N⁺(C₂H₅)₃Cl⁻ (25) | 1 | 100 |
| 3 | (n-C₁₆H₃₃)-N⁺⟨pyridine⟩ Cl⁻ (10) | 3 | 65 |
| 4 | (n-C₁₆H₃₃)₃N⁺CH₃Cl⁻ (5) | 5 | 60 |

*Percent yield is based on theoretical maximum.

Similar results were obtained using benzene as the solvent in place of methylene chloride.

No reaction was observed when the reactants were contacted under the same conditions as set forth in Example 1 but without the quaternary ammonium catalyst.

Other quaternary ammoniums can likewise be used. Similarly, other O,O-dialkyl pyridyl phosphorates and phosphorothioates can be prepared in excellent yields and purity by using the appropriate reactants. E.g., O,O-dimethyl O-3,5,6-trichlorophenyl phosphorate is prepared by reacting under alkaline conditions sodium 3,5,6-trichlorophenate with O,O-dimethyl phosphorochloridothioate in the presence of benzyltriethylammonium chloride or tetra-n-butylammonium bisulfate in a suitable inert liquid medium, such as methylene chloride or benzene.

We claim:

1. In the process of preparing a compound corresponding to the formula $$R-O-\overset{\overset{S}{\|}}{\underset{O-R_1}{P}}-O-R_2, \quad R-O-\overset{\overset{S}{\|}}{\underset{O-R_1}{P}}-C_6H_5 \text{ or}$$

$$R_2-O-\overset{\overset{S}{\|}}{\underset{R_1-O}{P}}-O-C_6H_4-S-C_6H_4-O-\overset{\overset{S}{\|}}{\underset{O-R_1}{P}}-O-R_2,$$

wherein: R₁ and R₂ are each independently lower alkyl; and

R is ⟨pyridinyl⟩—(X)ₙ wherein:
n is 0, 1, 2 or 3; and
X is nitro, cyano, halo, lower alkyl, lower alkoxy, lower alkylthio or lower alkylsulfinyl, with the proviso that R does not bear more than one nitro group, lower alkylthio group or lower alkylsulfinyl group;

by reacting in an inert organic liquid medium under alkaline conditions and with efficient blending (a) a compound corresponding to the formula $R-O^-M^+$ or $M^{+-}O-C_6H_4-S-C_6H_4-O^-M^+$ in solid particulate form with (b) a compound dissolved in said liquid medium and corresponding to the formula

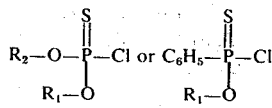

wherein M is an alkali metal and R, $R_1$ and $R_2$ have the aforesaid meaning;

the improvement consisting of conducting the process in the presence of a small but catalytic amount of a quaternary ammonium salt having a minimum solubility of at least 1 weight percent in the liquid reaction medium at 25°C and having a total aggregate carbon content of at least about 10 carbon atoms.

2. The process defined in claim 1 wherein (1) is a quaternary ammonium salt of the formula $R_1'R_2'R_3'R_4'N^+A^-$, wherein $R_1'-R_4'$ are each independently hydrocarbyl groups of from 1 to about 12 carbon atoms, or $R_1'$ is joined with $R_2'$ to form a 5- or 6-membered heterocyclic ring wherein one member of said heterocyclic ring is a quaternized nitrogen atom, a second member of said heterocyclic ring is an atom of carbon, nitrogen, oxygen or sulfur, and the remaining members of said heterocyclic ring are carbon atoms; and $A^-$ is an anion; said quaternary ammonium salt having a maximum carbon content of about 31 carbon atoms.

3. The process defined in claim 2 wherein said quaternary ammonium salt is a benzyltrimethyl-, benzyltriethyl-, or tetra-n-butylammonium salt.

4. The process defined in claim 3 wherein said quaternary ammonium salt is benzyltriethylammonium chloride or tetra-n-butylammonium bisulfate.

5. The process defined in claim 1 wherein said ammonium salt is present in an amount of from about 0.25 to about 20 mole percent, based on the combined moles of (a) and (b).

6. The process defined in claim 5 wherein the amount of said ammonium is from about 0.5 to about 10 mole percent.

7. The process defined in claim 1 wherein $R_1$ and $R_2$ are methyl or ethyl.

8. The process defined in claim 7 wherein R is

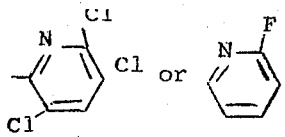

9. The process defined by claim 8 wherein said quaternary ammonium catalyst is a benzyltrimethyl-, benzyltriethyl- or tetra-n-butylammonium salt and is present in an amount of from about 0.25 to about 20 mole percent.

10. The process defined in claim 1 wherein said quaternary ammonium catalyst is benzyltriethylammonium chloride or tetra-n-butylammonium bisulfate and is present in an amount of from about 0.5 to about 10 mole percent.

11. The process defined in claim 10 wherein said process is conducted in methylene chloride.

12. The process defined in claim 1 wherein (a) is sodium O-3,5,6-trichloro-2-pyridinate and (b) is O,O-diethyl phosphorochloridothioate; and the reaction temperature is from about 40° to about 60°C.

* * * * *